US010495658B2

(12) United States Patent
Makino et al.

(10) Patent No.: US 10,495,658 B2
(45) Date of Patent: *Dec. 3, 2019

(54) AUTOMATIC ANALYZER

(71) Applicant: Hitachi High-Technologies Corporation, Tokyo (JP)

(72) Inventors: Akihisa Makino, Tokyo (JP); Mitsuhiro Hishinuma, Tokyo (JP); Toshiyuki Shimamori, Tokyo (JP); Masato Ishizawa, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 142 days.

This patent is subject to a terminal disclaimer.

(21) Appl. No.: 15/467,303

(22) Filed: Mar. 23, 2017

(65) Prior Publication Data

US 2017/0192027 A1 Jul. 6, 2017

Related U.S. Application Data

(63) Continuation of application No. 14/890,253, filed as application No. PCT/JP2014/063144 on May 19, 2014, now Pat. No. 9,709,588.

(30) Foreign Application Priority Data

Jun. 17, 2013 (JP) .................................. 2013-126248

(51) Int. Cl.
*G01N 35/04* (2006.01)
*G01N 35/10* (2006.01)
(Continued)

(52) U.S. Cl.
CPC ..... *G01N 35/1065* (2013.01); *G01N 35/0095* (2013.01); *G01N 35/00871* (2013.01);
(Continued)

(58) Field of Classification Search
None
See application file for complete search history.

(56) References Cited

U.S. PATENT DOCUMENTS

| 2004/0186360 A1 | 9/2004 | Suzuki |
| 2008/0271546 A1 | 11/2008 | Miller |
| 2011/0271773 A1 | 11/2011 | Komatsu |

FOREIGN PATENT DOCUMENTS

| JP | 3930977 B2 | 6/2007 |
| JP | 2008-3010 A | 1/2008 |

(Continued)

OTHER PUBLICATIONS

Machine generated English translation of Jp 2008-3010, pp. 1-15, published Jan. 10, 2008.*

(Continued)

*Primary Examiner* — Kathryn Wright
(74) *Attorney, Agent, or Firm* — Mattingly & Malur, PC

(57) ABSTRACT

An automatic analyzer with high processing capacity is capable of immediately measuring an emergency specimen rack. The automatic analyzer includes a conveying line for conveying a specimen rack, and an analysis unit which has a dispensing line in which a plurality of specimen racks are arranged for waiting until sample dispensing, and a sampling area for dispensing the sample to the analysis unit. A rack save area is provided in the dispensing line and at a position adjacent to the upstream side of the sampling area. When a specimen rack exists in the sampling area at the time of measuring an emergency specimen rack, a controller moves the specimen rack to the save area and positions the emergency specimen rack to be moved from a downstream side of the sampling area to the sampling area.

10 Claims, 6 Drawing Sheets

(51) Int. Cl.
   *G01N 35/02*   (2006.01)
   *G01N 35/00*   (2006.01)
(52) U.S. Cl.
   CPC .......... *G01N 35/02* (2013.01); *G01N 35/025* (2013.01); *G01N 35/026* (2013.01); *G01N 35/10* (2013.01); *G01N 2035/00801* (2013.01); *G01N 2035/00831* (2013.01); *G01N 2035/0462* (2013.01); *G01N 2035/0465* (2013.01); *G01N 2035/0496* (2013.01); *G01N 2035/1051* (2013.01)

(56) References Cited

FOREIGN PATENT DOCUMENTS

| JP | 2008-281453 A | 11/2008 |
| WO | 2007139212 A1 | 12/2007 |
| WO | 2008/133708 A1 | 11/2008 |
| WO | 2010/087303 A1 | 8/2010 |
| WO | 2011008972 A1 | 1/2011 |

OTHER PUBLICATIONS

International Search Report of PCT/JP2014/063144.
Extended European Search Report received in corresponding European Application No. 14813997.5 dated Feb. 16, 2017.

* cited by examiner

AUTOMATIC ANALYZER

CROSS REFERENCE TO RELATED APPLICATION

This application is a continuation application of U.S. application Ser. No. 14/890,253, filed Nov. 10, 2015, the entirety of the contents and subject matter of all of the above is incorporated herein by reference.

TECHNICAL FIELD

The present invention relates to an automatic analyzer for analyzing a component amount included in a sample such as blood and urine, and specifically, to an automatic analyzer having a plurality of analysis modules arranged along a conveying line of a specimen rack.

BACKGROUND ART

An automatic analyzer for clinical examination automatically analyzes and examines an instructed analysis item relative to a specimen (sample) such as blood, blood plasma, serum, urine, and other body fluid. As the automatic analyzer, a stand-alone-type analyzer which is operated as an independent device and a modular-type analyzer which connects analysis units in a plurality of analysis fields such as biochemistry and immunity by using a specimen rack conveying line in order to rationalize a work of an examination room and operates it as a single device have been known. The modular-type automatic analyzer has the plurality of analysis units for analyzing reaction liquid which has been made by mixing and reacting the sample with a reagent. As a method for supplying the sample to the analysis unit, there is a method for positioning the specimen rack for storing the sample container at a sample suction position of the analysis unit via the conveying line. Since the specimen rack is normally conveyed and analyzed in an order of conveyance from a rack supplying unit by the conveying line, to convey an emergency specimen which needs to be analyzed as soon as possible to the analysis unit with higher priority is an issue.

Regarding this issue, PTL 1 proposes a technique for supplying the specimen rack to the analysis unit by a disk-type rotatable specimen rack waiting unit according to the priority of the analysis Also, regarding an issue to improve processing capacity of the device, an automatic analyzer has been known which makes the plurality of specimen racks wait in a dispensing line of the analysis unit. PTL 2 introduces a technique for changing the number of specimen racks, which wait in the dispensing line, according to a mode such as a normal mode and an emergency mode.

Also, an automatic analyzer in PTL 3 includes a rack switching unit. When the analysis of the emergency specimen rack is requested, sample dispense is stopped even when the sample of a normal specimen rack is dispensed, and the specimen rack is returned to the rack switching unit, and then, an emergency specimen rack is supplied from the rack switching unit to the sampling area. In this way, the automatic analyzer copes with the measurement with high urgency.

CITATION LIST

Patent Literatures

PTL 1: JP 2008-281453 A
PTL 2: JP 3930977 B2
PTL 3: WO 10/087303 A

SUMMARY OF INVENTION

Technical Problem

In the technique disclosed in PTL 1, there has been a problem in that an operation for storing the specimen rack during sampling to the specimen rack waiting unit again and putting the emergency specimen in the sampling area is poor in swiftness. Also, since a single conveying line in which the specimen can reciprocate connects between the rack waiting unit and the sampling area and the specimen rack is switched at every sampling, improvement in the processing capacity of the device has been limited.

Also, with the technique disclosed in PTL 2, since a condition that the device is required is normally changed moment to moment, it is difficult to cope with a case where the analysis of the emergency specimen which needs to be measured as soon as possible is requested at the time of normal mode analysis.

Also, in the technique disclosed in PTL 3, the rack switching unit is connected to the sampling area with the single conveying line, and the specimen rack comes and goes between the rack switching unit and the sampling area. Therefore, it is difficult to improve the processing capacity. It can be considered to place an emergency rack conveying line for conveying only a specimen rack with high urgency. However, complication of the device and increase in the device cost will be a problem. An idea can be considered in which the rack switching unit and the sampling are used in common. However, the rack switching unit having a plurality of slots as disclosed in PTL 3 needs a large space, and a rack switching operation interferes with the sample dispensing operation. Therefore, it is also difficult to improve the processing capacity.

Regarding the modular-type automatic analyzer, a method for maintaining high processing capacity and immediately measuring an emergency specimen rack without complication of a device and increase in a device cost has been required.

Solution to Problem

The representative embodiment of the present invention will be described as follows.

An automatic analyzer includes: a conveying line configured to convey a specimen rack which stores a specimen container for holding a specimen; a plurality of analysis units configured to have a dispensing line in which the plurality of specimen racks arranged along the conveying line and waiting for sample dispensing is capable of waiting and to analyze and measure components included in the specimen; a sampling area configured to dispense the sample to the analysis unit; an identification device configured to be provided in the conveying line on the upstream side of the analysis unit and to read analysis request information relative to the specimen; and a controller configured to determine a conveyance path of the specimen rack from the analysis request information read by the identification device, and a rack save area is provided in the dispensing line and at a position adjacent to the upstream side of the sampling area, and when the specimen rack exists in the sampling area at the time of measuring an emergency specimen, the controller moves the specimen rack to the save area and positions an emergency specimen rack from the downstream side of the sampling area to the sampling area.

The specimen rack can be conveyed by using any methods which can move the rack such as a belt conveyor system and a pushing-out arm system for pushing out and moving a rear end of the rack.

With the configuration of the present invention, a conventional modular-type automatic analyzer with a high processing capacity can promptly analyze an emergency specimen without adding a new mechanism.

Advantageous Effects of Invention

An object of the present invention is to provide an automatic analyzer with high processing capacity which can immediately measure an emergency specimen rack while reducing complication of a device and increase in a device cost.

DESCRIPTION OF EMBODIMENTS

An embodiment of the present invention will be described in detail below with reference to the drawings. In all the figures to describe the embodiment, components having the same function are denoted with the same symbol as a general rule, and repeated description on the component will be omitted as much as possible. When one or more specimen containers can be mounted on the specimen rack, the number of the mounted specimen containers is not limited.

Figure 1:
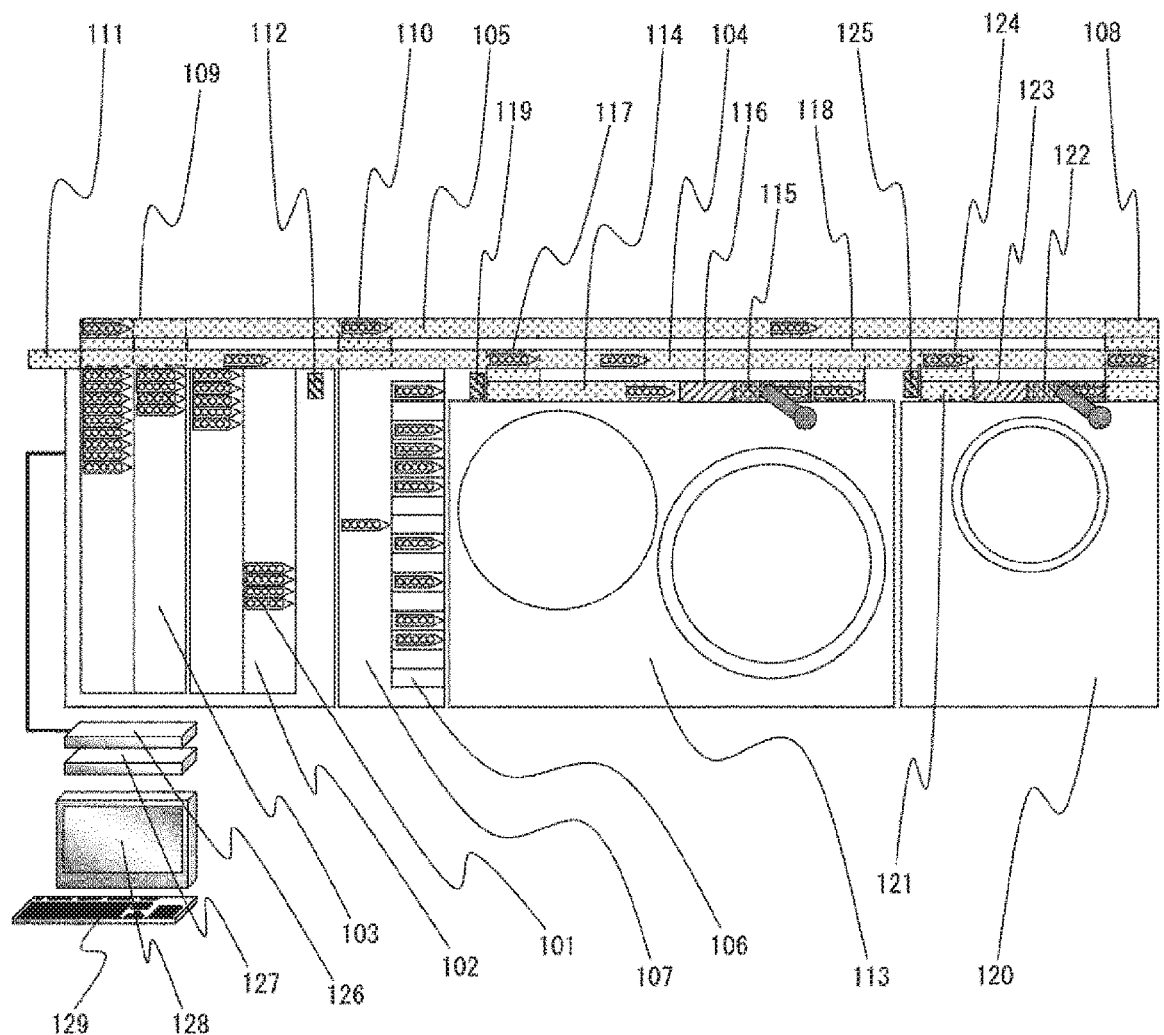
FIG. 1 is a schematic diagram of a modular-type automatic analyzer which is one embodiment of the present invention.
Figure 2:
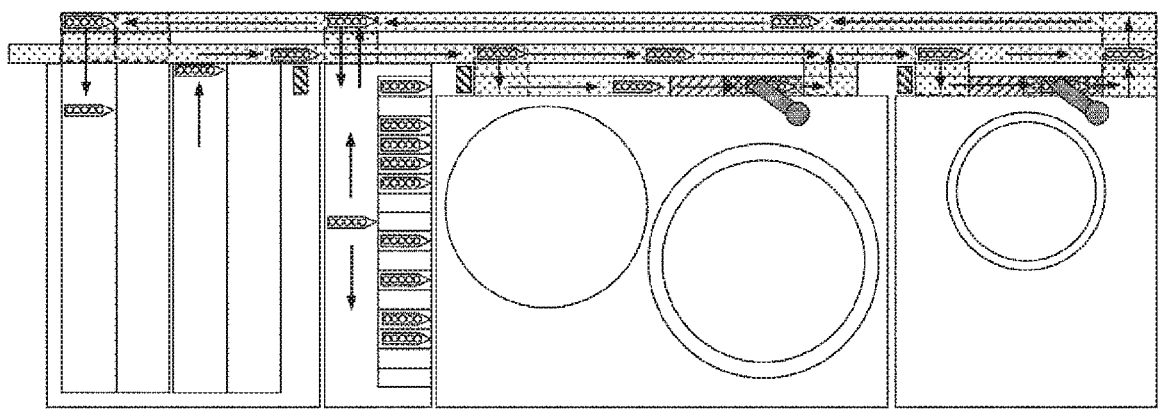
FIG. 2 is a schematic diagram of a conveyance path of a specimen rack at the time of normal analysis according to one embodiment of the present invention.

FIG. 1 is a schematic diagram of a modular-type automatic analyzer which is one embodiment of the present invention. FIG. 2 is a schematic diagram of a conveyance path of a specimen rack at the time of normal analysis.

A first analysis unit 113 arranged along a conveying line (first conveyance line or conveyance line) 104 includes an identification device 119 to collate analysis request information relative to a sample stored in a specimen rack 101, a rack take-in mechanism 117 for receiving the specimen rack 101 from the conveying line 104, a sampling area 115 for dispensing a sample in a sample container of the specimen rack 101, a dispensing line (second conveyance line) 114 having a role for conveying the specimen rack 101 to the sampling area 115 and making the specimen rack 101 wait for start of the dispensing, a rack save area 116 for saving the specimen rack 101 at the time of emergency specimen sampling, and a rack handling mechanism 118 for returning the specimen rack 101 after sampling to the conveying line 104 again.

A second analysis unit 120 is arranged along the conveying line 104 and arranged adjacent to the first analysis unit 113. Similarly to the first analysis unit 113, the second analysis unit 120 includes an identification device 125, a rack take-in mechanism 124, a sampling area 122, a dispensing line 121, and a rack save area 123.

A biochemical analysis unit is considered as an exemplary analysis unit. An exemplary configuration of the biochemical analysis unit includes a reaction disk for proceeding a reaction of a sample with a reagent in reaction vessels circumferentially aligned and arranged according to various analysis items, a reagent disk for operating such that the reagent according to each analysis item is positioned at a reagent suction position, a sample dispensing mechanism for dispensing the sample in the sample container from the sampling area 115 to the reaction vessel on the reaction disk, and a reagent dispensing mechanism for dispensing the reagent according to the analysis item from a reagent bottle on the reagent disk to the reaction vessel on the reaction disk. It is preferable to arrange the analysis unit which generally has a high specimen processing capacity on the upstream side in order to prevent congestion of the specimen racks 101.

Figure 4:
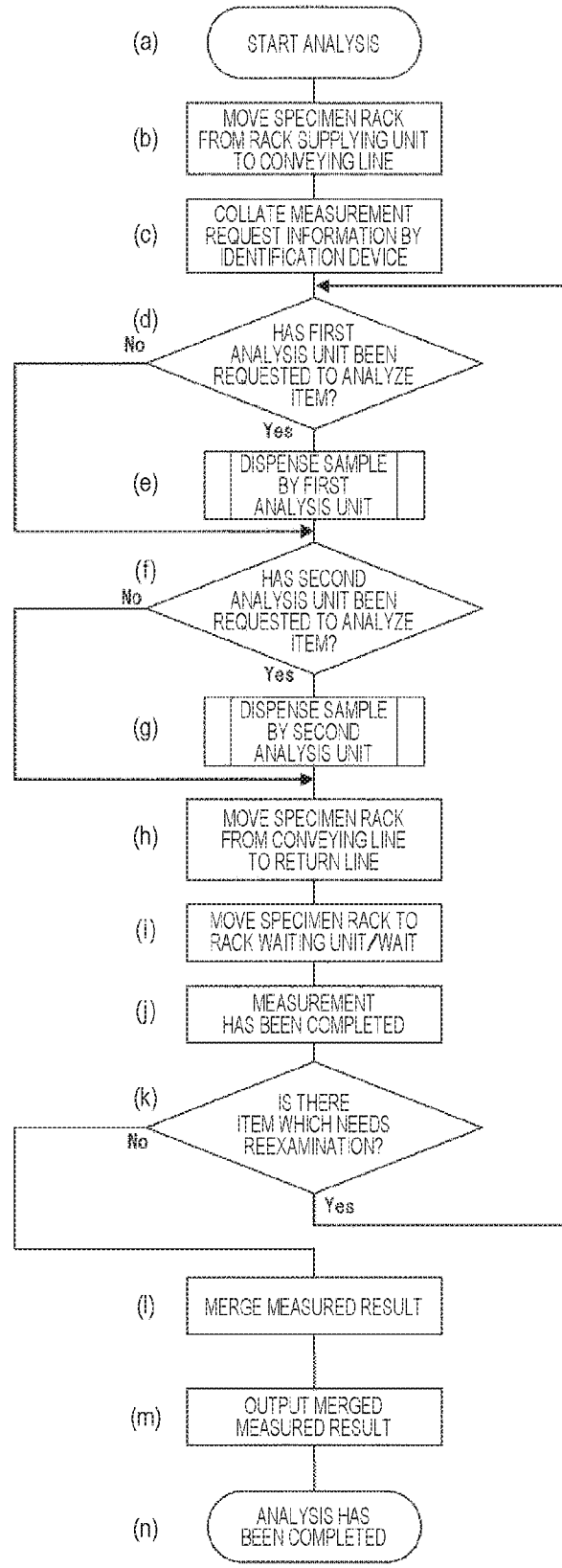
FIG. 4 is a flowchart of a normal analysis operation according to one embodiment of the present invention.
Figure 5:
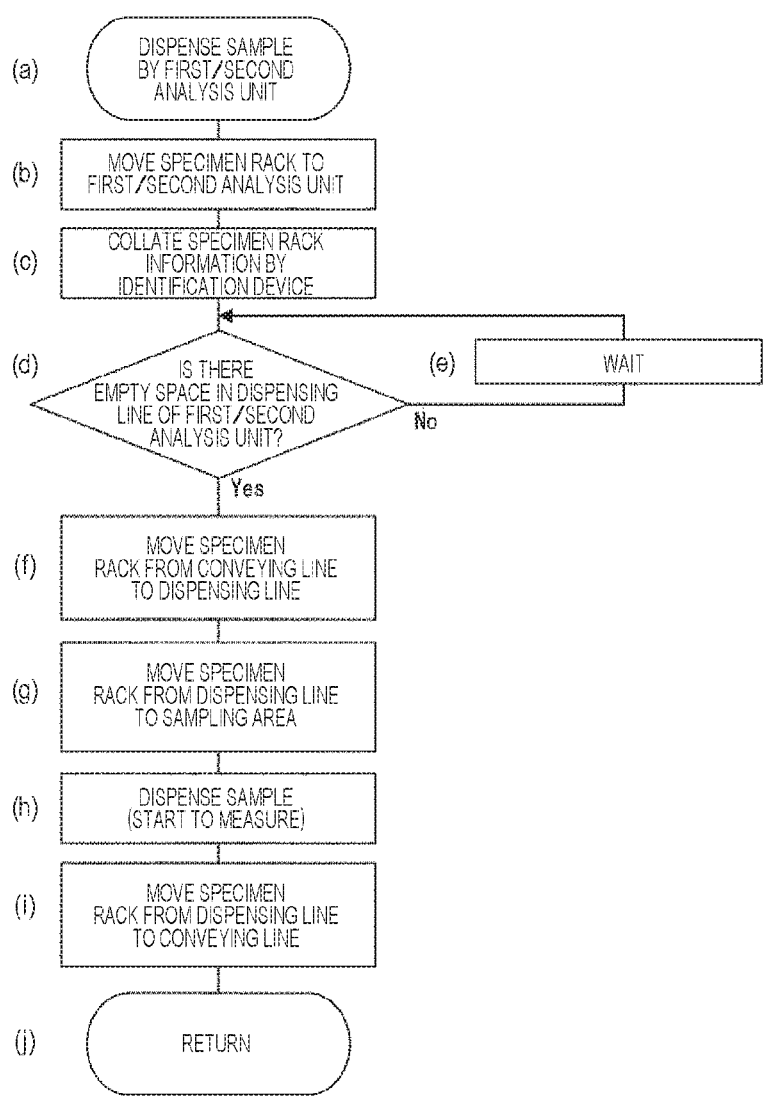
FIG. 5 is a flowchart of a sample dispensing operation of an analysis unit at the time of the normal analysis according to one embodiment of the present invention.

FIG. 4 is a flowchart of a normal analysis operation, and FIG. 5 is a flowchart of a sample dispensing operation of the analysis unit at the time of normal analysis. The conveyance path of the specimen racks 101 at the time of the normal analysis will be described with reference to FIGS. 2, 4, and 5.

When an input unit 129 requests an analysis, the analysis starts. A specimen rack number and a sample container number of the specimen rack 101 are recognized by reading an identification medium such as bar code labels attached on the specimen rack 101 and the sample container stored in the specimen rack 101 by an identification device 112 after the specimen rack 101 arranged in a rack supplying unit 102 has been transferred on the conveying line 104. Then, measurement request information is collated ((a) to (c) in FIG. 4). The specimen rack number and the sample container number recognized by the identification device 112 are transmitted to a controller 126, the type of the specimen rack 101, the kind of the analysis item instructed to each sample container, and the like are collated with analysis information which has been corresponded to a specimen receipt number and has been previously instructed by the input unit 129. The controller 126 determines a destination of the specimen rack 101 based on the collation result, and the destination is stored in a storage unit 127 and is used for processing to the specimen rack 101 after that.

When there is a sample to which the analysis by the first analysis unit 113 has been requested ((d) and (e) in FIG. 4), the specimen rack 101 is conveyed to the identification device 119 of the first analysis unit 113, and the identification device 119 collates specimen rack information (analysis information) ((a) to (c) in FIG. 5). When there is an empty space in the dispensing line of the first analysis unit, the rack take-in mechanism 117 transfers the specimen rack 101 from the conveying line 104 to the dispensing line 114. When there is no empty space, the specimen rack 101 waits at that place ((d) to (f) in FIG. 5). The transferred specimen rack 101 is moved to the sampling area 115, and the sample is dispensed to the reaction vessel by inserting a dispensing nozzle of a specimen dispensing mechanism to the sample container to which the analysis has been instructed ((g) and (h) in FIG. 5). When examinations on two or more items have been instructed to the single sample container, and when an examination item has been instructed to another sample container on the same specimen rack 101, a sample collecting operation is subsequently repeated.

The specimen rack 101, of which the samples regarding all the analysis items which have been instructed to the first analysis unit have been collected, is moved to a position where the rack handling mechanism 118 can cope with and is transferred on the conveying line 104 by the rack handling mechanism 118 ((i) and (j) in FIG. 5).

When there is a sample to which the analysis by the second analysis unit 120 has been requested ((f) and (g) in FIG. 4), as illustrated in FIG. 5, the specimen rack 101 is conveyed to the identification device 125 of the second analysis unit 120. Then, the identification device 125 collates specimen rack information (analysis information), and the rack take-in mechanism 124 transfers the specimen rack 101 from the conveying line 104 to the dispensing line 121. The transferred specimen rack 101 is moved to the sampling area 122, and the sample is dispensed to the reaction vessel by inserting the dispensing nozzle of the specimen dispensing mechanism into the sample container to which the analysis has been instructed. When the examinations on two or more items have been instructed to the single sample container, and when the examination item has been instructed to another sample container on the same specimen rack 101, the sample collecting operation is subsequently repeated ((a) to (i) in FIG. 5).

The specimen rack 101, of which the samples regarding all the analysis items which have been instructed to the second analysis unit have been collected, is moved to a position where the rack handling mechanism 108 can cope with and is moved to a return line 105 by the rack handling mechanism 108 ((h) in FIG. 4), and then, the specimen rack 101 is conveyed to a rack sorting mechanism 110 by the return line 105.

Since the specimen rack number of the conveyed specimen rack 101 has been stored in the storage unit 127, the controller 126 has already determined whether the specimen rack 101 is a specimen rack which needs no reexamination, such as a rack for control specimen, a rack for a standard sample, and a rack for cleaning liquid, or the specimen rack 101 is a specimen rack which has possibility to have the reexamination. Based on the determination, when there is no need for reexamination, the specimen rack 101 is moved to a rack returning mechanism 109 by the rack sorting mechanism 110 which has received a control signal of the controller 126 and stored in a rack storing unit 103 by the rack returning mechanism 109. When there is a possibility to have the reexamination, the specimen rack 101 is transferred to a waiting unit handling mechanism 107, is conveyed to a rack waiting unit 106, and waits for the determination regarding necessity of the reexamination ((i) in FIG. 4).

On the other hand, the sample collected in the reaction vessel on the reaction disk of the analysis unit is reacted with the reagent dispensed by the reagent dispensing mechanism, and data corresponding to each analysis item measured after a predetermined time is output to the controller 126 ((j) in FIG. 4). The controller 126 collates a determination standard which has been previously set with the analysis examination data. When the measured data is not proper, the storage unit 127 stores that the specimen needs reexamination as corresponding it to the specimen rack number and the sample container number ((k) in FIG. 4). The specimen rack 101, which has determined that there is no need to have the reexamination, is moved from the rack waiting unit 106 to the return line 105 by the waiting unit handling mechanism 107 and conveyed to the rack returning mechanism 109 by the return line 105. Then, the specimen rack 101 is stored in the rack storing unit 103 by the rack returning mechanism 109. Regarding first analysis examination data and analysis examination data of the reexamination, the measured result is merged, and the merged measured result is output (display) to a display 128 ((l) to (n) in FIG. 4).

The specimen rack 101 which has been determined by the controller 126 that it is necessary to have the reexamination based on the measured result of the first analysis unit 113 and the second analysis unit 120 is moved from the rack waiting unit 106 to the conveying line 104 by the waiting unit handling mechanism 107 and is conveyed to the first analysis unit 113 or the second analysis unit 120. The specimen rack 101 is analyzed in accordance with the above-mentioned procedure.

Figure 3:
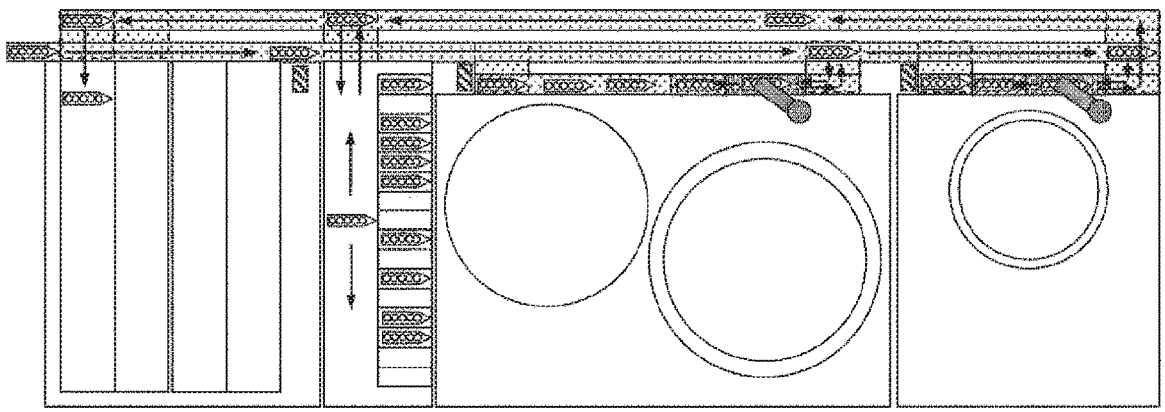
FIG. 3 is a schematic diagram of a conveyance path of an emergency specimen rack according to one embodiment of the present invention.
Figure 6:
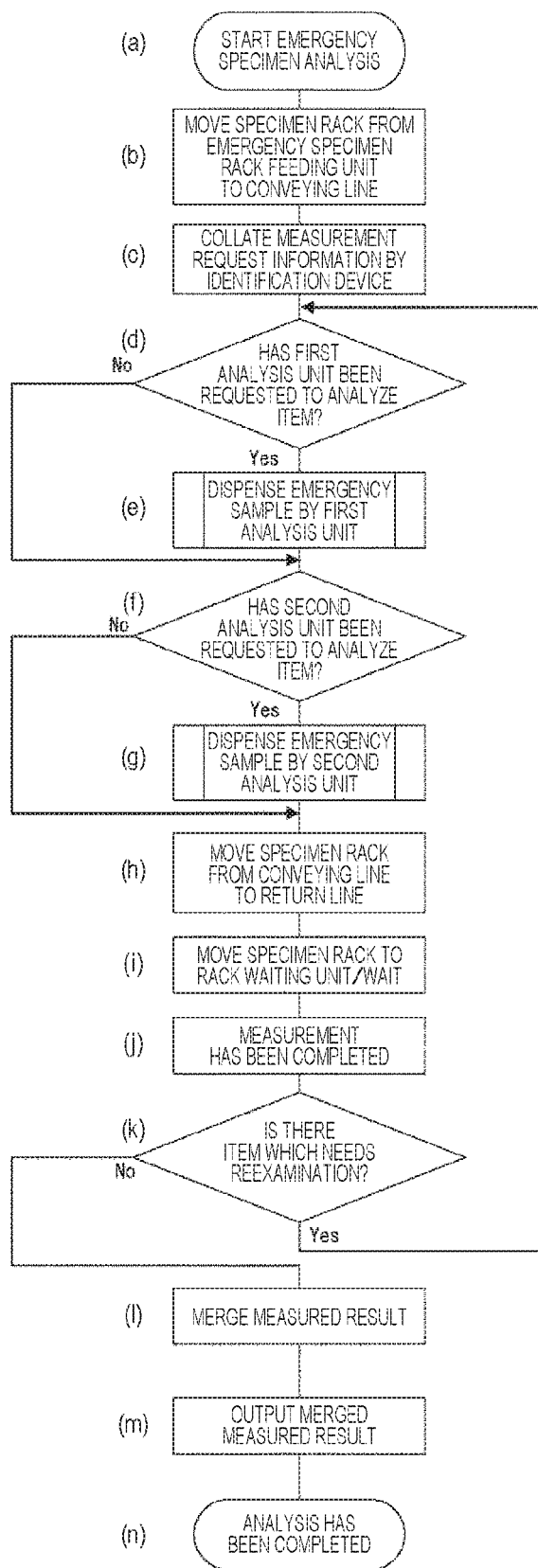
FIG. 6 is a flowchart of an emergency specimen analysis operation according to one embodiment of the present embodiment.
Figure 7:
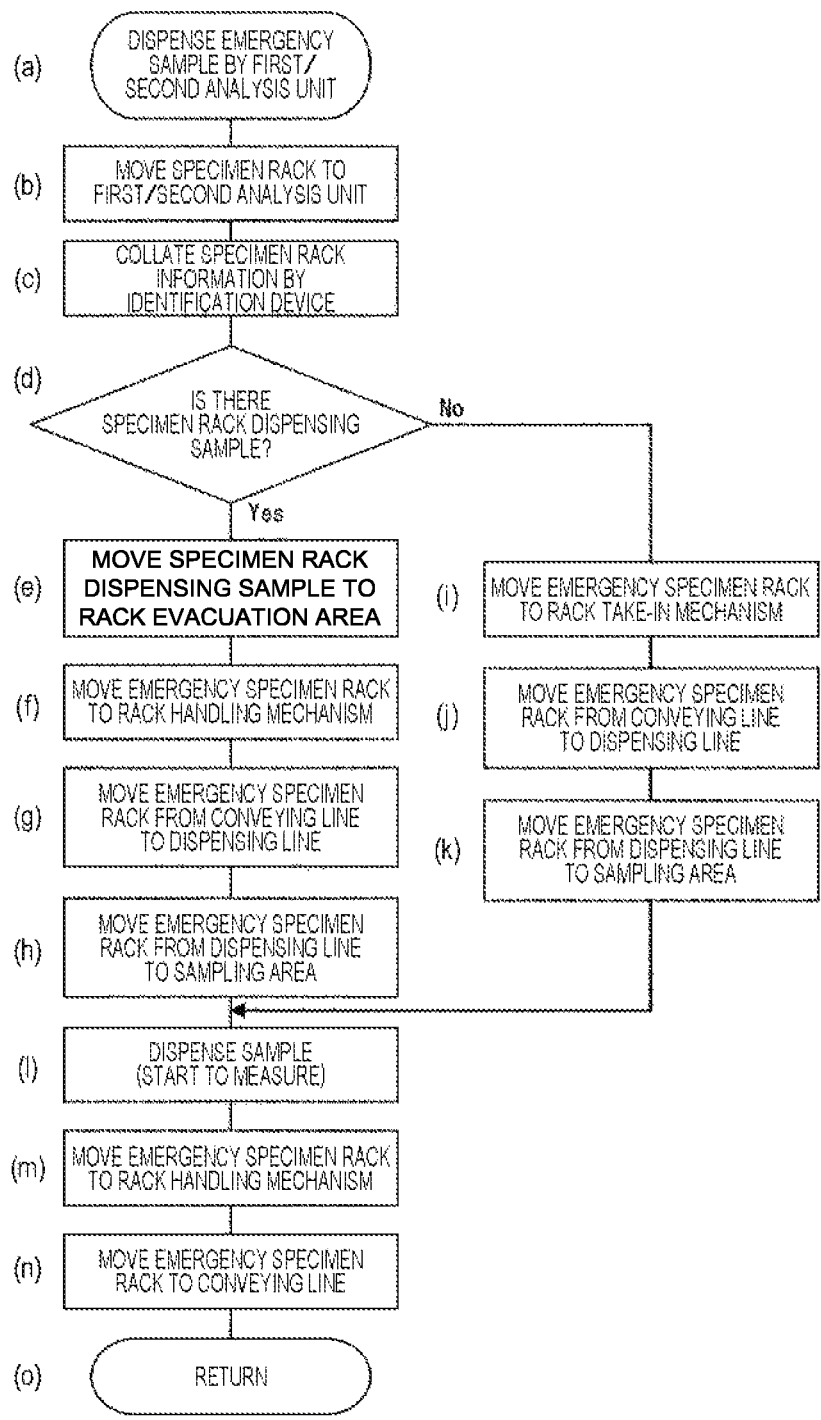
FIG. 7 is a flowchart of a sample dispensing operation of an analysis unit at the time of the emergency specimen analysis according to one embodiment of the present invention.

FIG. 3 is a schematic diagram of a conveyance path of an emergency specimen rack according to one embodiment of the present invention. FIG. 6 is a flowchart of an emergency specimen analysis operation. FIG. 7 is a flowchart of a sample dispensing operation of the analysis unit at the time of emergency specimen analysis. The conveyance path of the specimen rack 101 at the time of the emergency specimen analysis will be described with reference to FIGS. 3, 6, and 7. In FIG. 2, the specimen rack is conveyed in the dispensing line from the upstream to the downstream. Whereas, in FIG. 3, the emergency specimen rack is conveyed so as to be positioned in the sampling area from the downstream side of the sampling area. FIG. 2 is different from FIG. 3 at this point.

When the input unit 129 requests the emergency specimen analysis, the analysis starts. When the specimen rack 101 is placed on an emergency specimen rack feeding unit 111, the specimen rack 101 on the emergency specimen rack feeding unit 111 is transferred to the conveying line 104 in priority to the specimen rack 101 existing in the rack supplying unit 102 ((a) and (b) in FIG. 6). The specimen rack number and the sample container number are recognized by reading an identification medium such as a bar code label attached to the specimen rack 101 and the sample container stored in the specimen rack 101 by the identification device 112 after the specimen rack 101 has been transferred to the conveying line 104. Then, the measurement request information is collated ((c) in FIG. 6). The specimen rack number and the sample container number recognized by the identification device 112 are transmitted to the controller 126, and the type of the specimen rack 101, the kind of the analysis item instructed to each sample container, and the like are collated with analysis information which has been corresponded to the specimen receipt number and has been previously instructed by the input unit 129. The controller 126 determines a destination of the specimen rack 101 based on the collation result, and the destination is stored in the storage unit 127 and is used for processing to the specimen rack 101 after that.

When there is a sample to which the analysis by the first analysis unit 113 has been requested ((d) and (e) in FIG. 6), the specimen rack 101 is conveyed to the identification device 119 of the first analysis unit 113, and the identification device 119 collates specimen rack information (analysis information) ((a) to (c) in FIG. 7). When it is confirmed whether the specimen rack 101 dispensing the sample exists in the sampling area 115 ((d) in FIG. 7) and the specimen rack 101 does not exist, the specimen rack 101 is conveyed to a position, where the rack take-in mechanism 117 can cope with, by the conveying line 104 ((i) in FIG. 7). The specimen rack 101 stopped on the conveying line 104 is transferred to the dispensing line 114 by the rack take-in mechanism 117, and the transferred specimen rack 101 is moved to the sampling area 115. Then, the sample is dispensed to the reaction vessel by inserting the dispensing nozzle of the specimen dispensing mechanism into the sample container to which the analysis has been instructed ((j) to (l) in FIG. 7).

When the specimen rack 101 exists in the sampling area 115, the sampling area 115 is made empty by retreating the specimen rack 101 in the sampling area 115 to the rack save area 116 ((e) in FIG. 7). The specimen rack 101 having the emergency specimen mounted thereon is conveyed to the rack handling mechanism 118 by the conveying line 104 and moved to the dispensing line 114 by a rack handling mechanism (f) and (g) in FIG. 7). The specimen rack 101 is moved to the sampling area 115 by the dispensing line 114, and the sample is dispensed to the reaction vessel by inserting the dispensing nozzle of the specimen dispensing mechanism into the sample container to which the analysis has been instructed ((h) and (l) in FIG. 7).

In this way, when the rack save area 116 is provided in the dispensing line 114 and at a position adjacent to the upstream side of the sampling area 115 and the specimen rack exists in the sampling area 115 at the time of measuring the emergency specimen, the controller 126 moves the specimen rack to the rack save area 116 and positions the emergency specimen rack from the downstream side of the sampling area 115 to the sampling area. Accordingly, an automatic analyzer with high processing capacity which can immediately measure an emergency specimen rack while reducing complication of a device and increase in a device cost can be provided. As described above, when the specimen rack does not exist in the sampling area 115 at the time of measuring the emergency specimen, the controller 126 positions the emergency specimen rack from the upstream side of the sampling area to the sampling area.

Also, the specimen rack 101 during sampling and the specimen rack 101 having the emergency specimen mounted thereon may be separately moved. Also, after the specimen rack 101 having the emergency specimen mounted thereon has been moved to the dispensing line, both specimen racks 101 may be moved at the same time. That is, the specimen rack in the sampling area 115 and the emergency specimen rack may be moved to the upstream side in the dispensing line at the same time, and the specimen rack in the sampling area 115 and the emergency specimen rack may be respectively moved to the rack save area 116 and the sampling area. Accordingly, two specimen racks can be moved from the downstream side to the upstream side in the dispensing line by a single line control operation, and the two specimen racks can be more effectively moved than a case where the two specimen racks are separately moved.

In order to move the two specimen racks by the single line control operation, it is preferable that a space for a single specimen rack be provided on the dispensing line so that the rack handling mechanism 118 transfers the emergency specimen rack on the dispensing line 114 even when the specimen rack is positioned in the sampling area 115. Also, a space where at least a single specimen rack can wait is provided in the rack save area 116.

Also, it is necessary to perform processing so as to realize the above control in a normal condition. That is, the controller 126 controls a stopping position of the specimen rack in the dispensing line so that the specimen rack does not stop in the rack save area 116, and accordingly, the specimen rack existing in the sampling area 115 can move to the rack save area.

Therefore, the specimen racks may be moved so that a space for a single specimen rack is provided on the upstream side of the rack save area in the dispensing line as the interval between the specimen racks conveyed to the dispensing line. Also, in order not to provide the space for the rack save area, a known rack stopper may be provided immediately before the rack save area on the upstream side to prevent the entry of the rack. Also, when the dispensing line is configured of a single line, it is considered that the specimen rack immediately before the rack save area on the upstream side is concurrently retreated to the time when the specimen rack is positioned in the rack save area. To avoid such retreat, a known rack stopper may be provided on the upstream side of the specimen rack so that the specimen rack immediately before the rack save area of the specimen rack is not retreated to the upstream side in the dispensing line. In order to prevent the specimen rack from moving forward and entering the rack save area at the same time when the specimen rack is moved from the rack save area to the sampling area 115, it is effective to provide a known rack stopper in this case.

The specimen rack 101, of which the samples regarding all the analysis items which have been instructed have collected, is moved to a position where the rack handling mechanism 118 can cope with and is transferred on the conveying line 104 by the rack handling mechanism 118 ((m) to (o) in FIG. 7).

When the analysis by the second analysis unit 120 has been requested, the specimen rack 101 is conveyed to the second analysis unit. According to the similar operation to the above, the specimen rack 101 is conveyed, and the sample is dispensed to the second analysis unit ((f) and (g) in FIG. 6).

The specimen rack 101, of which the samples regarding all the analysis items which have been instructed have collected, is moved to a position where the rack handling mechanism 108 can cope with, is moved to the return line 105 by the rack handling mechanism 108 ((h) in FIG. 6), and is conveyed to the rack sorting mechanism 110 by the return line 105.

When the conveyed specimen rack 101 does not need to have the reexamination, the conveyed specimen rack 101 is moved to the rack returning mechanism 109 by the rack sorting mechanism 110 which has received the control signal from the controller 126 and stored in the rack storing unit 103 by the rack returning mechanism 109. When there is a possibility to have the reexamination, the specimen rack 101 is transferred to the waiting unit handling mechanism 107 and moved to the rack waiting unit 106. Then, the specimen rack 101 waits until the necessity of the reexamination is determined ((i) in FIG. 6). The controller 126 collates the determination standard which has been previously set with the analysis examination data. When the measured data is not proper, the storage unit 127 stores that the specimen needs reexamination as corresponding it to the specimen rack number and the sample container number ((k) in FIG. 6). The specimen rack 101, which has determined that there is no need to have the reexamination, is moved from the rack waiting unit 106 to the return line 105 by the waiting unit handling mechanism 107 and is conveyed to the rack returning mechanism 109 by the return line 105. Then, the specimen rack 101 is stored in the rack storing unit 103 by the rack returning mechanism 109. Regarding the first analysis examination data and the analysis examination data of the reexamination, the measured result is merged, and the merged measured result is output (display) to the display 128 ((l) to (n) in FIG. 6).

With the configuration according to the present embodiment, an automatic analyzer with high processing capacity which can immediately measure an emergency specimen rack while reducing complication of a device and increase in a device cost can be provided.

A case has been described in which an identification device is provided in each analysis unit. However, the identification device 112 may have the role without providing the identification device in each analysis unit. Also, the rack supplying unit, the rack storing unit, and the rack waiting unit have been described with reference to FIG. 1. However, they are not essential components in the present invention, and the present invention can be applied to a device which does not have the supplying unit, storing unit, and the waiting unit provided therein.

REFERENCE SIGNS LIST 101 specimen rack
102 rack supplying unit
103 rack storing unit
104 conveying line
105 return line
106 rack waiting unit
107 waiting unit handling mechanism
108 rack handling mechanism
109 rack returning mechanism
110 rack sorting mechanism
111 emergency specimen rack feeding unit
112 identification device (conveying line)
113 first analysis unit
114 dispensing line (first analysis unit)
115 sampling area (first analysis unit)
116 rack save area (first analysis unit)
117 rack take-in mechanism (first analysis unit)
118 rack handling mechanism (first analysis unit)
119 identification device (first analysis unit)
120 second analysis unit
121 dispensing line (second analysis unit)
122 sampling area (second analysis unit)
123 rack save area (second analysis unit)
124 rack take-in mechanism (second analysis unit)
125 identification device (second analysis unit)
126 controller
127 storage unit
128 display
129 input unit

The invention claimed is:

1. An automatic analyzer comprising:
a first conveyance line that conveys a plurality of specimen racks in a first direction;
an identification unit configured to obtain identification information from respective labels on the specimen racks on the first conveyance line;
a rack supplying unit that supplies one or more specimen racks, of the plurality of specimen racks, to the first conveyance line, which respectively store a specimen;
a second conveyance line, including a sampling area, that conveys respective specimen racks in the first direction from an upstream side to a downstream side to position the specimen rack in the sampling area and in a second direction from the downstream side to the upstream side;
an analysis unit having a reaction disk and a specimen dispensing mechanism which dispenses a respective specimen stored in a respective specimen rack positioned in the sampling area by the second conveyance line to the reaction disk;
a rack take-in mechanism configured to transfer specimen racks between the first conveyance line and the upstream side of the sampling area on the second conveyance line;
a rack handling mechanism configured to transfer specimen racks between the first conveyance line and the downstream side of the sampling area on the second conveyance line; and
a controller controlling the first conveyance line, the second conveyance line, the identification device and the specimen dispensing mechanism, wherein the controller is programed to:
control the identification device to obtain identification information from respective labels on respective specimen racks and determine whether the respective specimen racks store an ordinary sample or an emergency sample,
control the second conveyance line to convey a respective specimen rack determined to store an ordinary sample from an upstream side of the sampling area to a downstream side of the sampling area through the sampling area, and
upon determining a first specimen rack, of the plurality of specimen racks, stores an emergency sample and upon determining a second specimen rack, of the plurality of specimen racks, storing an ordinary sample is currently in the sampling area based on an operation of the specimen dispensing mechanism, control the second conveyance line to convey the second specimen rack holding the ordinary sample to a position on the second conveyance line that is upstream from the sampling area and control the second conveyance line to convey the first specimen rack holding the emergency sample from the first conveyance line to the sampling area from downstream of the sampling area.

2. The automatic analyzer according to claim 1, wherein the controller is further programmed to control the second conveyance line to convey the first specimen rack holding the emergency sample from the first conveyance line to the sampling area from downstream of the sampling area subsequent to controlling the second conveyance line to convey the second specimen rack holding the ordinary sample to a position on the second conveyance line that is upstream from the sampling area.

3. The automatic analyzer according to claim 1, wherein the controller is further programmed to control the second conveyance line to convey the second specimen rack holding the ordinary sample to a position on the second conveyance line that is upstream from the sampling area and simultaneously control the second conveyance line to convey the first specimen rack holding the emergency sample from the first conveyance line to the sampling area from downstream of the sampling area.

4. The automatic analyzer according to claim 1, wherein the controller is further programmed to:
upon determining the first specimen rack stores an emergency sample and upon determining the second specimen rack on the second conveyance line storing an ordinary sample is not currently in the sampling area based on an operation of the specimen dispensing mechanism control the second conveyance line to convey the first specimen rack to the sampling area from downstream of the sampling area.

5. An automatic analyzer comprising:
a conveyance line that conveys a plurality of specimen racks in a first direction;
an identification unit configured to obtain identification information from respective labels on the specimen racks on the conveyance line;
a dispensing line, including a sampling area, that conveys respective specimen racks in a first direction from a first position to a second position through a waiting area where the plurality of specimen racks wait, and conveys respective specimen racks in a second direction opposite the first direction from the second position through the sampling area to a first position side of the sampling area;
a reaction disk provided with a reaction container;
a specimen dispensing mechanism that dispenses a respective specimen stored in a respective specimen rack positioned in the sampling area by the dispensing line to a reaction container;
a reagent dispensing mechanism that dispenses a reagent to the reaction container;
a rack take-in mechanism configured to transfer specimen racks between the conveyance line and the upstream side of the sampling area on the dispensing line;
a rack handling mechanism configured to transfer specimen racks between the conveyance line and the downstream side of the sampling area on the dispensing line; and
a controller controlling the conveyance line, the dispensing line, the identification unit, and the specimen dispensing mechanism,
wherein the conveyance line is configured to convey respective specimen racks to the first position of the dispensing line and to the second position of the dispensing line, and
wherein the controller is programmed to:
control the identification device to obtain identification information from respective labels on respective specimen racks and determine whether the respective specimen racks store an ordinary sample or an emergency sample,
control the dispensing line to convey a respective specimen rack determined to store an ordinary sample from the first position of the dispensing line to the sampling area through the waiting area where the plurality of specimen racks wait, and to the second position of the dispensing line, and
upon determining a first specimen rack, of the plurality of specimen racks, stores an emergency sample and upon determining a second specimen rack, of the plurality of specimen racks, storing an ordinary sample is currently in the sampling area based on an operation of the specimen dispensing mechanism, control the dispensing line to convey the second specimen rack holding the ordinary sample in the second direction to the waiting position on the dispensing line and control the dispensing line to convey the first specimen rack holding the emergency sample in the second direction to the sampling area from the second position.

6. The automatic analyzer according to claim 5,
wherein the controller is further programmed to control the dispensing line to convey the first specimen rack holding the emergency sample from the conveyance line to the sampling area from second position subsequent to controlling the dispensing line to convey the second specimen rack holding the ordinary sample to the waiting area on the dispensing line.

7. The automatic analyzer according to claim 5,
wherein the controller is further programmed to control the dispensing line to convey the first specimen rack holding the emergency sample from the conveyance line to the sampling area from second position and simultaneously control the dispensing line to convey the second specimen rack holding the ordinary sample to the waiting area on the dispensing line.

8. An automatic analyzer comprising:
a first conveyance line that conveys a plurality of specimen racks in a first direction;
an identification unit configured to obtain identification information from respective labels on the specimen racks on the first conveyance line;
a rack supplying unit that supplies one or more specimen racks, of the plurality of specimen racks, to the conveyance line, which respectively store a specimen;
a second conveyance line, including a sampling area, that conveys respective specimen racks in a first direction from an upstream side to a downstream side to position the specimen rack in the sampling area and in a second direction opposite the first direction;
a reaction disk on which a reaction container is arranged;
a specimen dispensing mechanism which dispenses a specimen stored in a respective specimen container of the specimen rack positioned in the sampling area by the first rack conveying unit into a reaction container;
a reagent dispensing mechanism dispensing a reagent to the reaction container;
a rack take-in mechanism configured to transfer specimen racks between the first conveyance line and the upstream side of the sampling area on the second conveyance line;
a rack handling mechanism configured to transfer specimen racks between the first conveyance line and the downstream side of the sampling area on the second conveyance line; and
a controller controlling the first conveyance line, the second conveyance line, the identification device and the specimen dispensing mechanism,
wherein the first conveyance line is configured to convey respective specimen racks to downstream of the sampling area,
wherein the controller is programmed to:
upon determining a first specimen rack, of the plurality of specimen racks, stores an emergency sample and upon determining a second specimen rack, of the plurality of specimen racks, storing an ordinary sample is currently in the sampling area based on an operation of the specimen dispensing mechanism, control the second conveyance line to convey the second specimen rack holding the ordinary sample to a position on the second conveyance line that is upstream from the sampling area and control the second conveyance line to convey the first specimen rack holding the emergency sample from the first conveyance line to the sampling area from downstream of the sampling area.

9. The automatic analyzer according to claim 8,
wherein the controller is further programmed to control the second conveyance line to convey the first specimen rack holding the emergency sample from the first conveyance line to the sampling area from downstream of the sampling area subsequent to controlling the second conveyance line to convey the second specimen rack holding the ordinary sample to a position on the second conveyance line that is upstream from the sampling area.

10. The automatic analyzer according to claim 8, wherein the controller is further programmed to control the second conveyance line to convey the second specimen rack holding the ordinary sample to a position on the second conveyance line that is upstream from the sampling area and simultaneously control the second conveyance line to convey the first specimen rack holding the emergency sample from the first conveyance line to the sampling area from downstream of the sampling area.

\* \* \* \* \*